(12) United States Patent
Lee et al.

(10) Patent No.: US 11,264,211 B2
(45) Date of Patent: Mar. 1, 2022

(54) COLD PLASMA GENERATING APPARATUS AND MULTI-COLD PLASMA ARRAY APPARATUS COMPRISING THE SAME

(71) Applicant: PSM Inc., Gyeonggi-do (KR)

(72) Inventors: Keun-Ho Lee, Seoul (KR); Olivier Postel, Colorado Springs, CO (US)

(73) Assignee: PSM Inc., Gyeonggi-do (KR)

( * ) Notice: Subject to any disclaimer, the term of this patent is extended or adjusted under 35 U.S.C. 154(b) by 22 days.

(21) Appl. No.: 16/791,098

(22) Filed: Feb. 14, 2020

(65) Prior Publication Data
US 2021/0233746 A1 Jul. 29, 2021

(30) Foreign Application Priority Data
Jan. 29, 2020 (KR) .................. 10-2020-0010243

(51) Int. Cl.
*H01J 37/32* (2006.01)
*A61L 2/14* (2006.01)
*H05H 1/46* (2006.01)

(52) U.S. Cl.
CPC .......... *H01J 37/32201* (2013.01); *A61L 2/14* (2013.01); *H01J 37/3244* (2013.01); *H05H 1/46* (2013.01); *H05H 1/4622* (2021.05); *H05H 2245/36* (2021.05)

(58) Field of Classification Search
None
See application file for complete search history.

(56) References Cited

U.S. PATENT DOCUMENTS

| | | | | |
|---|---|---|---|---|
| 4,734,551 A | * | 3/1988 | Cheek | ................... C21C 5/5205 219/121.59 |
| 4,918,282 A | | 4/1990 | Cheek | |
| 2009/0065485 A1 | * | 3/2009 | O'Neill | ................... H05H 1/46 219/121.52 |
| 2010/0052539 A1 | * | 3/2010 | Choi | ........................ H05H 1/46 315/111.21 |
| 2010/0247403 A1 | | 9/2010 | Hancock | |
| 2010/0296977 A1 | | 11/2010 | Hancock | |
| 2013/0319460 A1 | | 12/2013 | Schneider et al. | |
| 2014/0066838 A1 | | 3/2014 | Hancock | |
| 2015/0056107 A1 | | 2/2015 | Hancock | |
| 2017/0232122 A1 | | 8/2017 | Hancock | |
| 2018/0318459 A1 | * | 11/2018 | Hancock | ............. H01J 37/3244 |
| 2018/0342379 A1 | * | 11/2018 | Jurczyk | ................. C23C 14/021 |

(Continued)

FOREIGN PATENT DOCUMENTS

| | | |
|---|---|---|
| CN | 2572245 Y | 9/2003 |
| CN | 101662880 A | 3/2010 |
| CN | 101918044 A | 12/2010 |

(Continued)

*Primary Examiner* — Amy Cohen Johnson
*Assistant Examiner* — James H Cho
(74) *Attorney, Agent, or Firm* — IP Legal Services, LLC (57) ABSTRACT

The present disclosure relates to a cold plasma generating apparatus that can efficiently ignite (initially discharge) cold plasma and easily match common impedance and that is optimized for use in applications related to sterilization because it can uniformly distribute power to multiple plasma sources through a single power supply in a multi-plasma array configuration and increase effective plasma volume, and a multi-cold plasma array apparatus comprising the same.

6 Claims, 5 Drawing Sheets

(56) References Cited

U.S. PATENT DOCUMENTS

2020/0171180 A1   6/2020   Hancock

FOREIGN PATENT DOCUMENTS

| | | |
|---|---|---|
| CN | 103533876 A | 1/2014 |
| CN | 106838981 A | 6/2017 |
| JP | 62-234654 A | 10/1987 |
| JP | 06188094 A * | 7/1994 |
| JP | 2007-157535 A | 6/2007 |
| KR | 10-0736218 B1 | 7/2007 |
| KR | 10-0786537 B1 | 12/2007 |
| KR | 10-2010-0024685 A | 3/2010 |
| KR | 10-1740821 B1 | 5/2017 |
| KR | 10-1940012 B1 | 1/2019 |
| KR | 10-2019-0035052 A | 4/2019 |

\* cited by examiner

COLD PLASMA GENERATING APPARATUS AND MULTI-COLD PLASMA ARRAY APPARATUS COMPRISING THE SAME

CROSS REFERENCE TO PRIOR APPLICATIONS

The present application claims priority under 35 U.S.C. § 119 to Korean Patent Application No. 10-2020-0010243 (filed on Jan. 29, 2020).

BACKGROUND

Field of the Invention

The present disclosure relates to a cold plasma generating apparatus and a multi-cold plasma array apparatus comprising the same, and more particularly, to a cold plasma generating apparatus that can efficiently ignite (initially discharge) cold plasma and easily match common impedance and that is optimized for use in applications related to sterilization because it can uniformly distribute power to multiple plasma sources through a single power supply in a multi-plasma array configuration and increase effective plasma volume, and a multi-cold plasma array apparatus comprising the same.

Related Art

Plasma has been widely used in surface treatment of semiconductor, display devices, and various parts, and is broadening its applicability and establishing itself as an emerging fusion technology used in biotechnology research, medicine, air purification, incinerators, etc.

That is, a plasma generator is generally a device that dissociates gas molecules between two electrodes into anions and electrons when the two electrodes are supplied with a high frequency or high voltage. The two electrodes may be installed in a vacuum or air. Such a plasma generator is applied in semiconductor, PCB, new material synthesis, polymer surface treatment, metal surface treatment, environmental purification, medical devices, food sterilization and disinfection, and so on, and its field of application is getting wider and wider.

Plasma is finding more and more applications, especially in medical fields such as tooth whitening, cancer cell killing, speeding the rate of blood clotting, and so on. Laser, which has been conventionally and generally used, is disadvantageous in that it can cause burns from thermal damage and cannot uniformly distribute light over a wide treatment area due to the small radius of the laser beam. On the other hand, plasma offers advantages such as causing no thermal damage and uniformly and efficiently treating a wide treatment area depending on the plasma generator.

It's reported that UV light, oxygen radicals such as ozone, nitrogen oxides such as nitric oxide, current, and electrically charged particles created from plasma provide benefits such as cell immunity boosting, sterilization, cancer cell necrosis, blood circulation boosting, and so on in the treatment of human diseases.

Such a plasma generator used for medical purposes requires stability since it applies plasma directly to a human body.

For instance, there is a need to prevent an electric shock due to the leakage of high voltage applied to generate a plasma. It is necessary to easily adjust the amount of plasma applied to prevent damage to the human body, or the amount of plasma emission needs to be easily adjusted to make plasma available in surgery by increasing the amount of plasma applied to burn a target tissue.

Moreover, user convenience and miniaturization are required to allow the user to easily handle the plasma generator. The miniaturization of the plasma generator and the easy adjustment of the amount of plasma emission are deemed necessary, especially in order to apply the plasma generator to a particular type of sterilization.

However, conventional plasma generators require high voltage to generate plasma, making insulation difficult. Another problem is that generating plasma at low powers for medical uses such as sterilization or cell treatment has its limitations because it is quite difficult to efficiently ignite an initial discharge and match impedance.

PRIOR ART DOCUMENTS

Patent Documents (Patent Document 0001) Korean Registered Patent Publication No. 10-0736218 (published on Jul. 6, 2007)
(Patent Document 0002) Korean Registered Patent Publication No. 10-0786537 (published on Dec. 18, 2007)
(Patent Document 0003) Korean Registered Patent Publication No. 10-1740821 (published on May 26, 2017)
(Patent Document 0004) Korean Registered Patent Publication No. 10-1940012 (published on Jan. 18, 2019)
(Patent Document 0005) Korean Laid-Open Patent Publication No. 10-2019-0035052 (filed on Apr. 3, 2019)

SUMMARY

The present disclosure provides a cold plasma generating apparatus that can efficiently ignite (initially discharge) plasma and easily match common impedance.

The present disclosure also provides a cold plasma generating apparatus that is optimized for use in applications related to sterilization because it can uniformly distribute power to multiple plasma sources through a single power supply and increase effective plasma volume.

Technical problems to be solved by the present disclosure are not limited to the above-mentioned technical problems, and other technical problems not mentioned herein may be clearly understood by those skilled in the art from description below.

In order to accomplish the above aspects and/or other features of the present invention, according to one aspect of the present disclosure, there is provided a cold plasma generating apparatus for generating a cold plasma source, the cold plasma generating apparatus comprising: an apparatus housing with a discharge hole formed at one end; a central conductor of conductive material provided along the longitudinal centerline of the apparatus housing; a nipple member provided at one side of the apparatus housing and connected to the cavity of the apparatus housing so that plasma gas enters the same; a microwave transmission member that extends integrally in a direction perpendicular to one side of the center conductor and transmits microwaves from a microwave generator to the center conductor; and an impedance matching adjustment member provided at the other end of the apparatus housing, for adjusting the length of the center conductor exposed to the cavity of the apparatus housing to minimize microwave reflection and match cavity impedance to a microwave source.

In one aspect of the present disclosure, the discharge hole of the apparatus housing may be larger than the outer diameter of the center conductor, and the outer diameter of the center conductor may be smaller than the diameter of the discharge hole.

In one aspect of the present disclosure, the microwave transmission member may have the same diameter as the center conductor and extend integrally and perpendicularly to the other end of the center conductor, and the microwave transmission member may have the same diameter as the apparatus housing and extend along the centerline of a tubular extension extending perpendicularly to the apparatus housing.

In one aspect of the present disclosure, the diameter of the center conductor may be ½ of that of the microwave transmission member, the diameter of the microwave transmission member may be ⅛ or less of the wavelength of the microwaves, and the length of the center conductor from the microwave transmission member to the other end of the apparatus housing may be one-half or whole of the wavelength of the microwaves.

In one aspect of the present disclosure, the impedance matching adjustment member may be configured as a knob-type adjustment member whose outer edge is threaded to the other end of the apparatus housing, and the other end of the center conductor may be contained in the impedance matching adjustment member so as to move in and out of the same.

In one aspect of the present disclosure, the distance between the center conductor and the impedance matching adjustment member relative to the microwave transmission member may be greater than one-quarter of the wavelength of the microwaves and less than one half of the wavelength of the microwaves.

According to another aspect of the present disclosure, there is provided a multi-cold plasma array apparatus comprising: a treatment chamber having an inner space; a treatment target containing member provided in the inner space of the treatment chamber, where a treatment target is placed; a rotary agitator configured to rotate the treatment target containing member; multiple cold plasma generating apparatuses according to any one of claims 1 to 6 arranged in the treatment chamber; an ignition unit configured to ignite the multiple cold plasma generating apparatuses; a power supply configured to supply power to the multiple cold plasma generating apparatuses; a power distribution unit configured to distribute the power supplied from the power supply uniformly to the multiple cold plasma generating apparatuses; and a gas circulation and supply unit configured to circulate and supply a gas or gas mixture to the treatment chamber.

In another aspect of the present disclosure, the treatment target containing member may be made of Teflon or fiberglass netting, the multiple cold plasma generating apparatuses may be arranged toward the center of the treatment chamber to face each other, and the ignition unit may comprise: a grounded box formed with a cradle in which each of the multiple plasma generating apparatuses is tightly held and mounted; a leaf spring that elastically supports the cold plasma generating apparatus and is electrically grounded to the grounded box; a push switch provided on one side of the grounded box which can be depressed; a relay provided on the push switch and comprising a shaft extendable by the push switch; an operating lever configured to be rotated by the shaft of the relay in such a manner that the other end thereof is connected to the output of the power supply as one end thereof moves towards the tip; and a tension spring configured to elastically return the operating lever to the original position.

In another aspect of the present disclosure, the power distribution unit may comprise: a nascent load that is connected to the power supply through a waveguide and receives initial microwave power from the power supply; a microwave circulator that is provided on the waveguide, receives microwave power from the power supply, and redirects reflected waves of the microwave power back to the nascent load; and a power splitter that receives the microwave power, splits the same in multiple ways, and transmits the same to each of the multiple plasma generating apparatuses, and the gas circulation and supply unit may comprise: a pumping device for pumping a gas and/or gas mixture out of the treatment chamber; a filtering device for filtering the gas pumped out by the pumping device; and a gas adding device that adds the gas filtered by the filtering device and the gas supplied from an external gas supply device and feeds the gases to the cold plasma generating apparatus.

A cold plasma generating apparatus and a multi-cold plasma array apparatus comprising the same offer the following advantages:

Firstly, the present disclosure has the advantage of providing a cold plasma generating apparatus that can efficiently ignite (initially discharge) low-temperature cold plasma and easily match common impedance.

Secondly, the present disclosure has the advantage of providing a small-sized and portable plasma generating apparatus by uniformly distributing power to multiple plasma sources through a single power supply.

Thirdly, the present disclosure has the advantage of increasing effective plasma volume because uniform low-temperature plasma is generated through multiple plasma sources.

Fourthly, the present invention has the advantage of providing a multi-cold plasma array apparatus optimized for use in applications related to sterilization.

The advantages of the present disclosure are not limited to the above-mentioned ones, and other advantages not mentioned herein may be clearly understood by those skilled in the art from description below

DETAILED DESCRIPTION OF EMBODIMENTS

Additional aspects, features, and advantages of the present disclosure will become apparent from the following description and accompanying figures.

Prior to a detailed description of the present disclosure, it should be understood that the present disclosure may be variously modified and may have various embodiment, and the examples described below and illustrated in the drawings are not intended to limit the present invention to specific embodiments and the present disclosure includes all changes, equivalents, or replacements included in the spirit and technical scopes of the present disclosure.

It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Terms used in the present specification are used only in order to describe specific exemplary embodiments rather than limiting the present invention. Singular forms are intended to include plural forms unless the context clearly indicates otherwise. It will be further understood that the terms "comprise" or "have" used in this specification, specify the presence of stated features, numerals, steps, operations, components, parts, or a combination thereof, but do not preclude the presence or addition of one or more other features, numerals, steps, operations, components, parts, or a combination thereof.

Furthermore, terms such as " . . . part", " . . . unit", and " . . . module" mean a unit which processes one or more functions or operations, and may be implemented by hardware, software, or a combination of hardware and software.

In the following description to be given with reference to the accompanying drawings below, the same components are designated by the same reference symbols, and redundant descriptions of these components will be omitted. In the following description of the embodiments, detailed descriptions of related known technologies will be omitted when they may unnecessarily make the gist of the present disclosure obscure.

In the whole specification of the present invention, it will be understood that when a step is referred to as being located "on" or "before" another step, it may have the same rights as not only in the case where the step is in a direct time series relationship with another step but also in the case of an indirect time series relationship in which the time series order of two steps can be changed as in the mixing step after each step.

Hereinafter, a cold plasma generating apparatus and a multi-cold plasma array apparatus comprising the same according to an exemplary embodiment of the present disclosure will be described in details with reference to the accompanying drawings.

Figure 1:
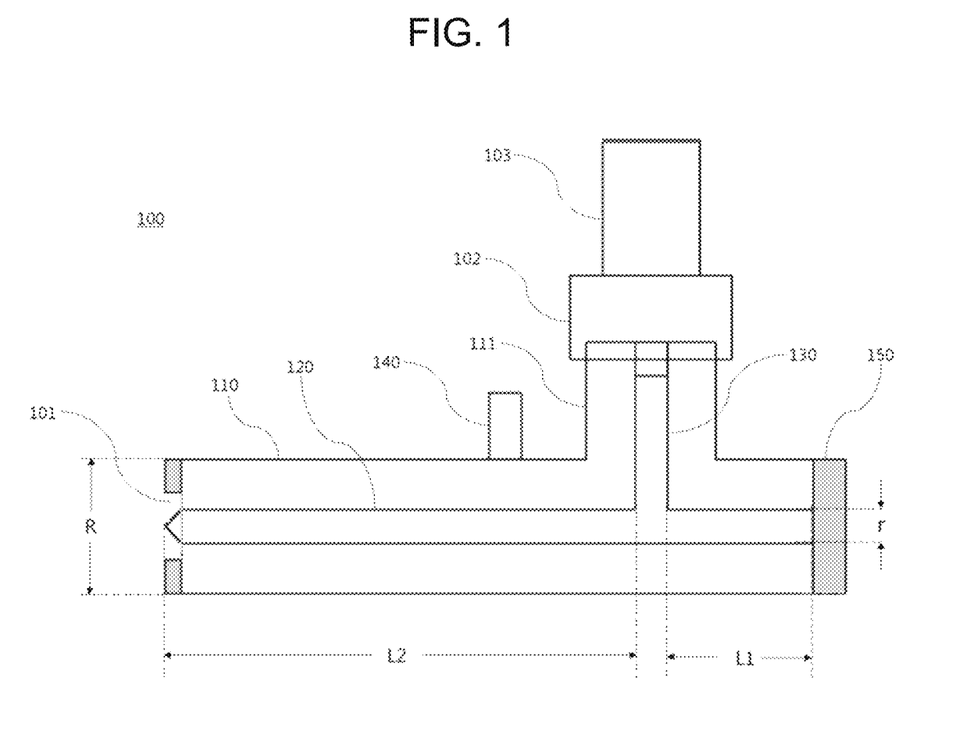
FIG. 1 is a schematic view showing a configuration of a cold plasma generating apparatus according to the present disclosure.

First of all, a cold plasma generating apparatus according to the present disclosure will be described in details with reference to FIG. 1. FIG. 1 is a schematic view showing a configuration of a cold plasma generating apparatus according to the present disclosure.

The cold plasma generating apparatus according to the present disclosure is an apparatus for generating a cold plasma source, which, as shown in FIG. 1, roughly comprises: an apparatus housing 110; a center conductor 120; a microwave transmission member 130; a nipple member 140; and an impedance matching adjustment member 150.

Concretely, the cold plasma generating apparatus according to the present disclosure is an apparatus for generating a cold plasma source, which, as shown in FIG. 1, comprises: a cylindrical or tubular apparatus housing 110 with a discharge hole 101 formed at one longitudinal end to discharge ionized gas; a central conductor 120 of conductive material provided along the longitudinal centerline of the apparatus housing 110; a microwave transmission member 130 that extends integrally and perpendicularly to one side of the center conductor 120 and transmits microwaves from a microwave generator (not shown) to the center conductor 120 in a cavity of the apparatus housing 110; a nipple member 140 provided at one side of the apparatus housing 110 and connected to the cavity of the apparatus housing 110 so that plasma gas enters the same; and an impedance matching adjustment member 150 provided at the other end of the apparatus housing 110, for adjusting the length of the center conductor 120 exposed to the cavity of the apparatus housing 110 to minimize microwave reflection and match cavity impedance to a microwave source.

More concretely, the cylindrical or tubular apparatus housing 110 has a cavity with a predetermined inner diameter R. Here, the cavity (i.e., the inside of the apparatus housing 110) serves as a quasi-resonant cavity.

Moreover, the discharge hole 101 of the apparatus housing 110 is larger than the outer diameter r of the center conductor 120, and, thus, plasma gas entering through the nipple member 140 flows around the center conductor 120, and the ionized plasma gas passes through the tip of the center conductor 120 and is discharged through the discharge hole 101.

That is, the gas is ionized at the tip of the center conductor 120 when the cavity of the apparatus housing 110 is excited by microwave fields, forming an ionized gas flow (G/F). The ionized gas flow (G/F) is relatively cold and has a high energy.

Moreover, the center conductor 120 is provided on the central axial line of the apparatus housing 110 and has a predetermined outer diameter r. Here, the outer diameter r of the center conductor 120 is smaller than the discharge hole 101 of the apparatus housing 110. In other words, the discharge hole 101 of the apparatus housing 110 is larger than the outer diameter r of the center conductor 120.

In addition, one end of the center conductor 120 is shaped as a sharp tip, and may protrude slightly from one end of the apparatus housing 110. Here, the protruding length (the amount of protrusion) of one end of the center conductor 120 may be adjusted when setting it up.

Next, the microwave transmission member 130 is made into a stub-like structure, which extends integrally and perpendicularly to one side of the center conductor 120, that is, which is formed integrally with the center conductor 120 at an angle of 90° from it.

The microwave transmission member 130 has the same diameter as the center conductor 120. The microwave transmission member 130 is a component that allows microwaves from the microwave generator (not shown) to be generated in the cavity of the apparatus housing 110.

In this case, the microwave transmission member 130 has the same diameter as the apparatus housing 110, and is provided inside an extension 111 extending perpendicularly to the apparatus housing 110, and the extension 111 is coaxially connected to a connecting line 103 of the microwave generator through a waveguide fitting 102. The waveguide fitting 102 serves as a means for it to be connected to the extension 111 to transmit the microwaves from the connecting line 103 to the cavity of the apparatus housing 110.

In the present disclosure, the center conductor 120 and the microwave transmission member 130 are made out of a highly electrically conductive material such as copper, brass, or silver.

Moreover, the nipple member 140 constitutes a component that is connected to allow plasma gas to enter the cavity of the apparatus housing 110 from a plasma gas supply device.

Preferably, the nipple member 140 is provided in front (on the gas discharge side) of the extension 111 when communicatively formed in the apparatus housing 110.

Here, the nipple member 140 for gas injection may be configured to intersect the cavity of the apparatus housing 110 or inject gas tangentially, as exemplified in the drawing. Also, it may be configured to inject gas in the lengthwise direction of the apparatus housing 110.

In addition, the gas may be an inert gas such as argon or helium or may be air such as a mixture of nitrogen, oxygen, and other gases.

Next, the impedance matching adjustment member 150 is provided on the other end of the apparatus housing 110 and configured in such a manner that the distance L1 between the center conductor 120 at one side of the microwave transmission member 130 and the impedance matching adjustment member 150 is adjusted relative to the microwave transmission member 130. Thus, the distance between the center conductor 120 exposed to the cavity of the apparatus housing 110 and the impedance matching adjustment member 150 is adjusted, thereby minimizing the microwave reflection in the cavity of the apparatus housing 110 and matching cavity impedance to the microwave source.

Concretely, the impedance matching adjustment member 150 is configured as an adjustment knob threaded to the other end of the apparatus housing 110, and the other end of the center conductor 120 is slidably contained in a center portion of the impedance matching adjustment member 150 (so as to move in and out of it). Here, the impedance matching adjustment member 150 and the other end of the center conductor 120 may be threaded together.

In this way, the impedance matching adjustment member 150 is provided on the other end of the apparatus housing 110, which adjusts the length L1 at which the other side of the center conductor 120 is exposed to the cavity of the apparatus housing 110 relative to the microwave transmission member 130.

The distance adjustment by the impedance matching adjustment member 150 is done in millimeters.

The distance adjustment in millimeters by the impedance matching adjustment member 150 allows for minimizing microwave reflection and matching cavity impedance to the microwave source.

The distance is greater than one-quarter of the wavelength of the microwaves used, but less than one half of the wavelength.

The distance L2 between one side of the center conductor 120 and one end of the apparatus housing 110 relative to the microwave transmission member 130 in the cavity of the apparatus housing 110 is an integral number of half wavelengths, but its length is one-half or whole of the wavelength of the microwaves used.

In the present disclosure, the microwave frequency may vary between 800 MHz and 50 GHz.

Moreover, the scaling of the geometry of the center conductor 120 and microwave transmission member 130 are such that the diameter of the center conductor 120 is about ½ of that of the microwave transmission member 130 and the diameter of the microwave transmission member 130 is typically ⅛ or less of the wavelength of the microwaves employed.

The plasma generating apparatus according to the present disclosure may be designed in a small size in such a manner that gas and power are fed to the head of the plasma generating apparatus through a supply line that is flexible enough to enable three-dimensional delivery and supply.

The ignition (initiation) of the plasma is achieved by discharging the ionized gas generated by a high-voltage or high-frequency discharge (spark) near the tip region of the apparatus housing 110.

Meanwhile, in a modification of the plasma generating apparatus according to the present disclosure, the impedance matching adjustment member 150 is formed as a cover cap-shaped structure and fixed to the other end of the apparatus housing 110, and the other end of the center conductor 120 is provided at the center of the cover cap-shaped structure to slide a predetermined length, rather than rotating the impedance matching adjustment member 150 so that the distance L1 between the center conductor 120 at one side of the microwave transmission member 130 and the impedance matching adjustment member 150 is adjusted relative to the microwave transmission member 130. Also, the waveguide fitting 102 is mated to the extension 111 in such a manner that the extension 111 slides in millimeters in the lengthwise direction of the apparatus housing 110. Thus, the distance between the other end of the center conductor 120 and the cover cap-shaped structure may be adjusted by moving the extension 111 forward in millimeters. As such, the length of the center conductor 120 exposed to the cavity of the apparatus housing 110 may be adjusted, thereby minimizing microwave reflection and matching cavity impedance to the microwave source.

Next, a multi-cold plasma array apparatus comprising the above-described cold plasma generating apparatus will be described in details with reference to FIGS. 2 to 5.

Figure 2:
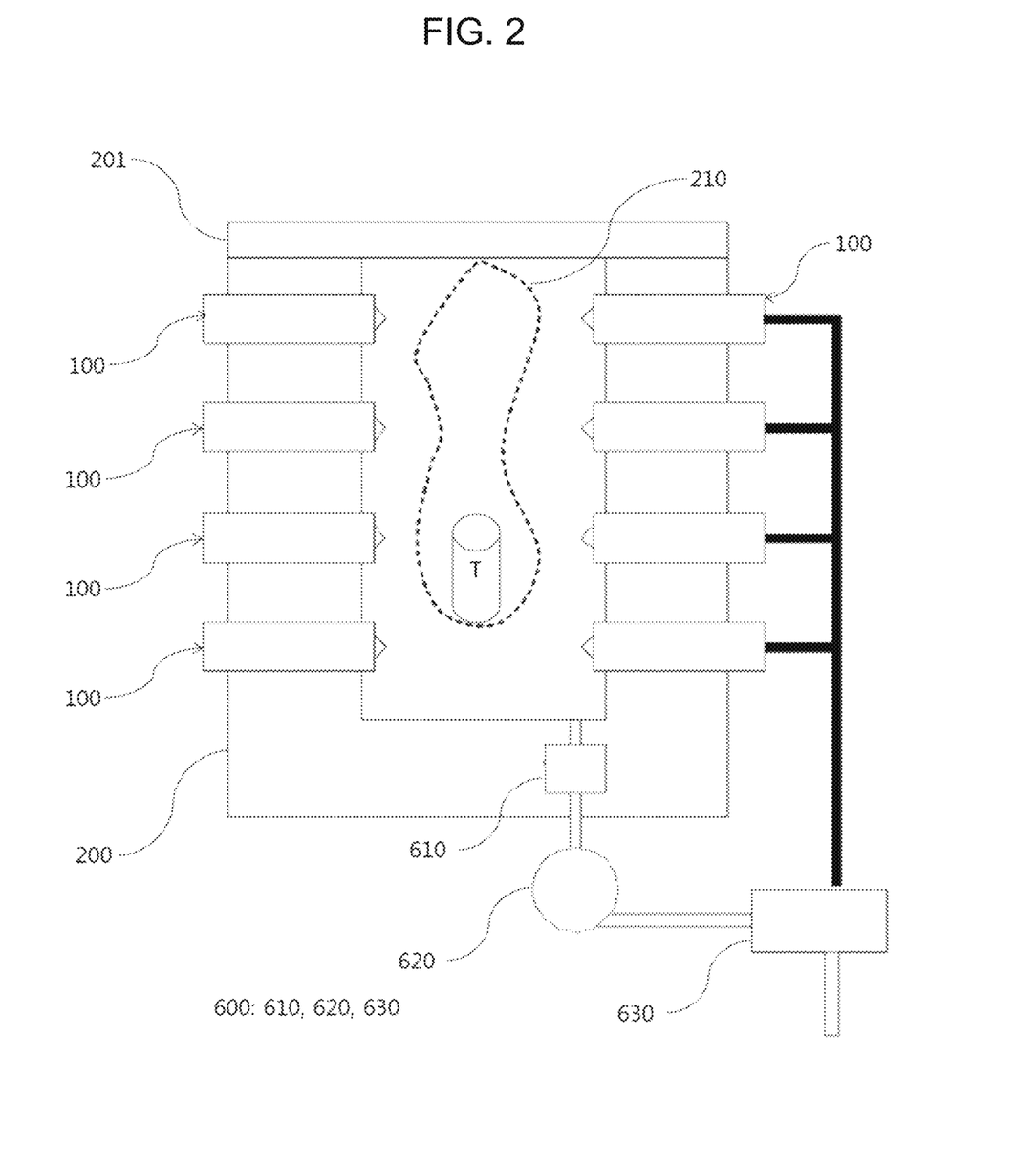
FIG. 2 is a schematic view showing a configuration of a multi-cold plasma array apparatus according to the present disclosure.
Figure 3:
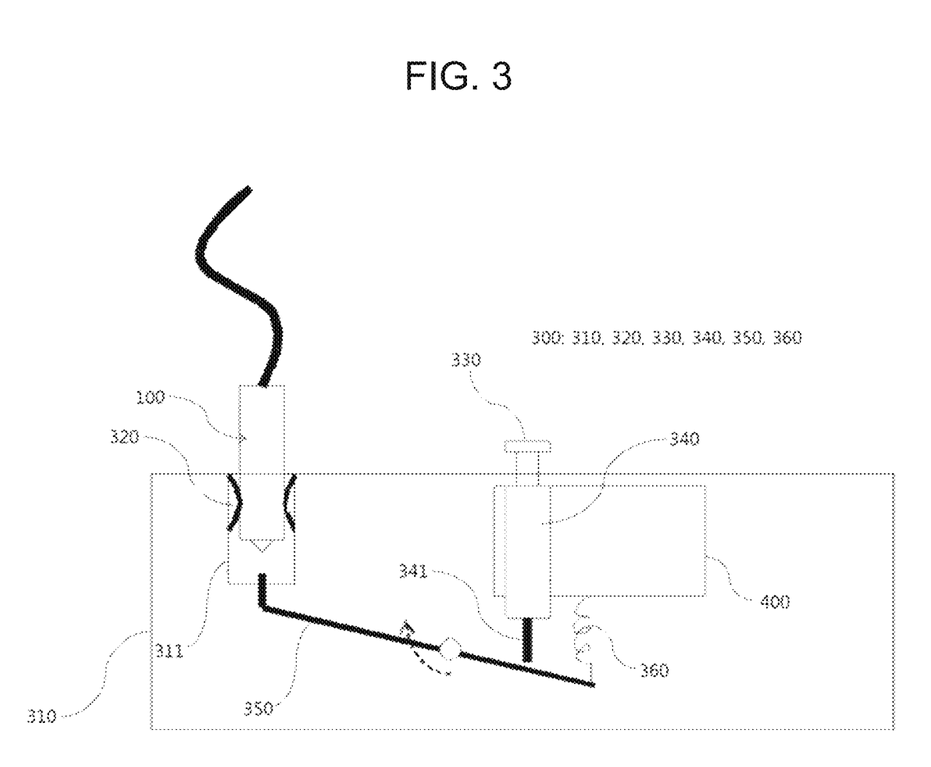
FIG. 3 is a schematic view explaining a configuration of an ignition unit included in the multi-cold plasma array apparatus according to the present disclosure to ignite a cold plasma source.
Figure 4:
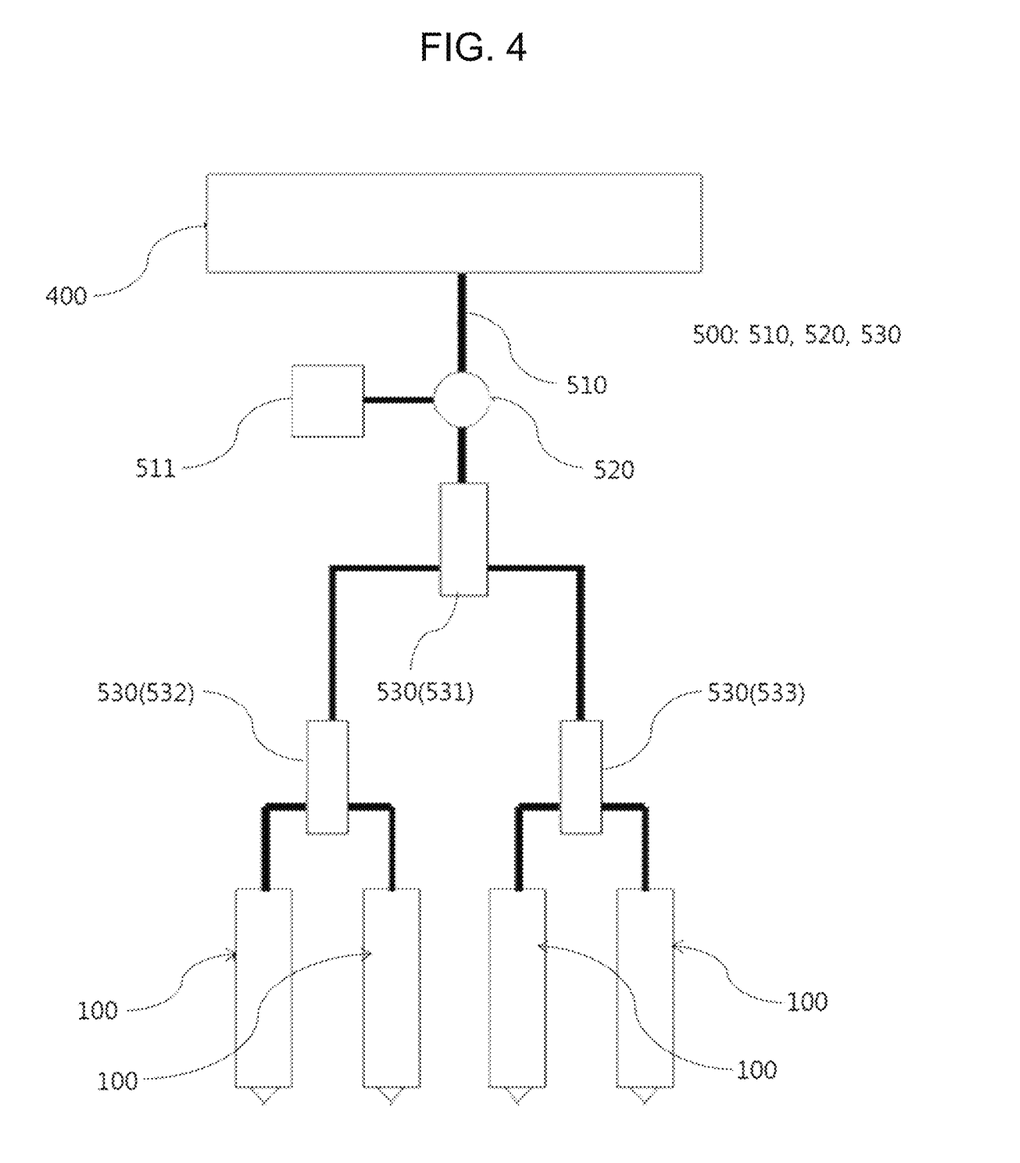
FIG. 4 is a schematic view explaining a configuration of a power distribution unit included in the multi-cold plasma array apparatus according to the present disclosure.
Figure 5:
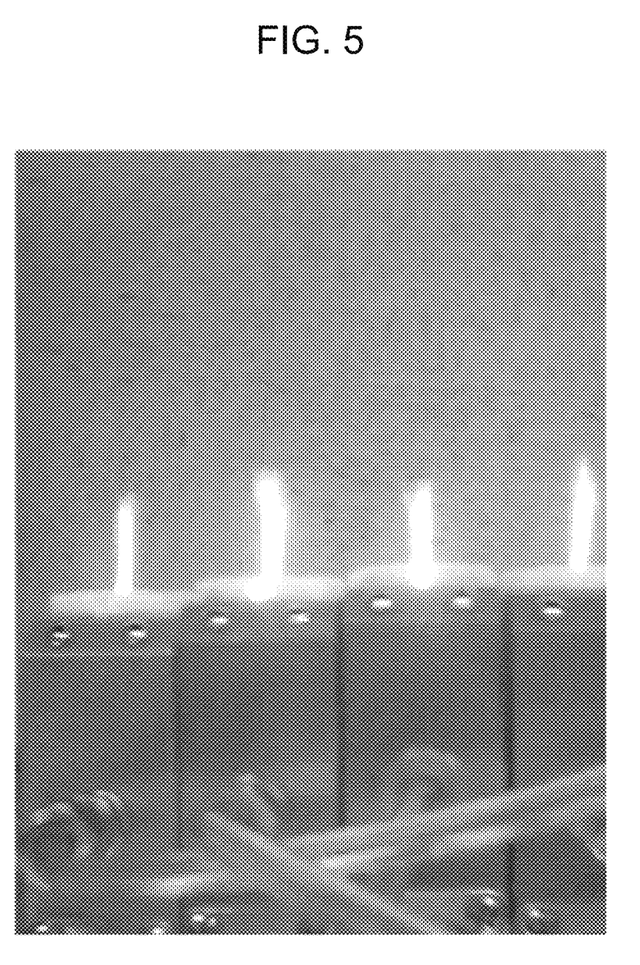
FIG. 5 is a photograph of an experiment in which microwave power is distributed from a single power supply to multiple plasma generating apparatuses, in the multi-cold plasma array apparatus according to the present disclosure.

FIG. 2 is a schematic view showing a configuration of a multi-cold plasma array apparatus according to the present disclosure. FIG. 3 is a schematic view explaining a configuration of an ignition unit included in the multi-cold plasma array apparatus according to the present disclosure to ignite a cold plasma source. FIG. 4 is a schematic view explaining a configuration of a power distribution unit included in the multi-cold plasma array apparatus according to the present disclosure. FIG. 5 is a photograph of an experiment in which microwave power is distributed from a single power supply to multiple plasma generating apparatuses, in the multi-cold plasma array apparatus according to the present disclosure.

Here, FIG. 4 shows an example of an environmentally controllable treatment chamber used in the sterilization of small objects with a size of 1 to 5 cm.

As shown in FIGS. 2 to 4, the multi-cold plasma array apparatus according to the present disclosure roughly comprises: the cold plasma generating apparatus 100; a cylindrical treatment chamber 200; a treatment target containing member 210; a rotary agitator; an ignition unit 300; a power supply 400; a power distribution unit 500; and a gas circulation and supply unit 600.

Concretely, as shown in FIGS. 2 to 4, the multi-cold plasma array apparatus according to the present disclosure comprises: a cylindrical treatment chamber 200 having an inner space containing a treatment target T and configured to keep it enclosed in a controlled environment; a treatment target containing member 210 provided in the inner space of the treatment chamber 200, where the treatment target T is placed; a rotary agitator (not shown) configured to rotate and agitate the treatment target containing member 210 so that a treatment surface of the treatment target T is directed in a predetermined direction; multiple cold plasma generating apparatuses 100 arranged on a wall surface of the treatment chamber 210 and brought into contact with the ground; an ignition unit 300 configured to ignite the multiple cold plasma generating apparatuses 100; a power supply 400 configured to supply required power to the multiple cold plasma generating apparatuses 100; a power distribution unit 500 configured to distribute the power supplied from the power supply 300 uniformly to the multiple cold plasma generating apparatuses 100; and a gas circulation and supply unit 600 configured to circulate and supply a gas or gas mixture to the treatment chamber 200.

The cylindrical treatment chamber 200 consists of an airtight vessel, and has an opening and closing door 201 at one side to contain the treatment target T in it.

The treatment target containing member 210 is made of Teflon or fiberglass netting, and the treatment target T is preferably suspended in the netting and aligned along the centerline of the treatment chamber 200, which allows the surface of the treatment target T to be uniformly exposed to cold plasma jets.

The rotary agitator may be configured as a well-known rotary mechanical agitator or rotating mechanism that can be rotated through electric and electronic control and positioned in a predetermined position.

A detailed description of the configuration of each of the multiple cold plasma generating apparatuses 100 will be omitted below as it will be redundant.

Still, it should be noted that, in the cold plasma generating apparatus according to the present disclosure, the multiple cold plasma generating apparatuses 100 are arranged on the treatment chamber 200 to face each other.

Accordingly, the multiple cold plasma generating apparatuses 100 are configured to discharge cold plasma jets toward the center of the treatment chamber 200.

Next, the ignition unit 300 will be described.

The ignition unit 300 is configured to ignite the multiple cold plasma generating apparatuses 100, which serves to ignite the cold plasma jet while it is safely stored in an electrically shielded box that minimizes electromagnetic interference.

Specifically, the ignition unit 300 comprises a grounded box 310 formed with a cradle 311 in which each of the multiple plasma generating apparatuses 100 is tightly held and mounted.

The cradle 311 of the grounded box 310 comprises a leaf spring that elastically supports the plasma generating apparatus 100 and is electrically grounded to the grounded box 310. The leaf spring 320 makes contact with the grounded box 310 which comprises an electrical starting circuit module (to be described later) initially charged by a high-voltage power supply 400.

The grounded box 310 comprises a push switch 330 which the user depresses to initiate the cold plasma jet.

The push switch 330 activates a relay 340, and the relay 340 extends a shaft 341 extendable by the relay 340 to rotate an operating lever 350 in such a manner that one end of the operating lever 350 comes into proximity with the tip of the plasma generating apparatus 100. The other end of the operating lever 350 is connected to the output of the high voltage power supply 400.

Once one end of the operating lever is in proximity with the tip of the plasma generating apparatus 100, a spark discharge occurs between the end of the operating lever 350 and the tip of the plasma generating apparatus 100.

As the push switch 330 is released, a tension spring 360 elastically returns the operating lever 350 to its original position.

Next, the power supply 400 is a microwave power supply which provides power to each plasma power generating apparatus 100 through the power distribution unit 500 to be described below.

The high-voltage power supply 400 can be a capacitor, charged to high potential by a battery. A resistor placed in series with the capacitor determines the time for the operating lever 350 to recharge to high potential.

Next, the power distribution unit 500 is configured to provide power uniformly to the multiple cold plasma generating apparatuses 100 arranged in the treatment chamber 200, for exposing the cold plasma jets across a large area.

The power distribution unit 500 comprises a nascent load 510 that is connected to the microwave power supply 400 through a waveguide 511 and receives initial power from the power supply 400.

Also, the power distribution unit 500 comprises a microwave circulator 520 that is provided on the waveguide 511, receives output power from the microwave power supply 400, and redirects any reflected power from the microwave power supply 400 back to the nascent load 510.

The microwave circulator 520 protects the power supply by returning reflected power.

Moreover, the power distribution unit 500 comprises a power splitter (two-way splitter) 530 (i.e., first power splitter 531) which receives the microwave power from the microwave power supply 400 and splits it in multiple ways (two ways in the drawing).

The power splitter 530, i.e., the first power splitter 531, is configured to branch balanced power off into two multiple paths (two paths in the drawing), and each path is connected to other multi-way splitters (i.e., second two-way splitter 532 and third two-way splitter 533).

Here, the paths (a total of four branches in the drawing) of each splitter 531 to 533 carry approximately equal power from all of the multiple plasma generating apparatuses 100 (a total of four plasma generating apparatuses in the drawing).

As such, the present disclosure may be implemented in more plasma generating apparatuses through a single power supply, and, in practice, limitations are placed by the power loading capabilities of the waveguide 511 and power splitters 531 to 533.

Next, the gas circulation and supply unit 600 is configured to circulate and supply (part of) the source gas and/or source gas mixture discharged from the treatment chamber 200 to the multiple plasma generating apparatuses 100.

Specifically, the gas circulation and supply unit 600 comprises a pumping device 610 for pumping a source gas and/or source gas mixture (hereinafter, abbreviated as "gas") out of the treatment chamber 200, a filtering device 620 for filtering the gas pumped out by the pumping device 610, and a gas/gas mixture adding device 630 that adds the gas filtered by the filtering device 620 and the gas supplied from an external gas supply device and feeds the gases to the head of the cold plasma generating apparatus 100.

The gas circulation and supply unit 600 filters the source gas and/or source gas mixture pumped by the pumping device 610 and discharged from the treatment chamber 200 through the filtering device 620, and then adds an external source gas or source gas mixture through the gas/gas mixture adding device 620 and supplies it to the head or top side of the cold plasma generating apparatus 100.

As described above, the cold plasma generating apparatus and multi-cold plasma array apparatus comprising the same can be ignited under atmospheric conditions by holding and manipulating them by hand to adjust to various surfaces of treatment targets to be sterilized, as needed by the user, thereby optimally exposing cold plasma (cold plasma jets) to the surfaces of the treatment targets to be sterilized or decontaminated.

Furthermore, the present disclosure allows for providing power through the above-described power distribution method and discharging an array of cold plasma jets to the atmosphere, and makes it more practical to discharge the array into an enclosed chamber.

Furthermore, the present disclosure enables recirculation of source gases such as argon through the gas circulation and supply unit and makes it more useful for systematic and reproducible sterilization.

Meanwhile, the cold plasma generating apparatus and multi-cold plasma array apparatus comprising the same allow for ultrasonically cleaning a treatment target prior to exposing it to plasma, in order to enhance sterilization.

Moreover, a UV lamp may be provided on a wall surface of the treatment chamber 200 to further enhance sterilization. As is well known, UV light is able to kill bacteria in the spectral range below 254 nm. The incorporation of the UV lamp is an enhancement of, but not a substitute for, the cold plasma jet.

As described above, the cold plasma generating apparatus and multi-cold plasma array apparatus comprising the same offer advantages such as providing a cold plasma source that can efficiently ignite (initially discharge) low-temperature plasma, and providing a small-sized and portable plasma generating apparatus by uniformly distributing power to multiple plasma sources through a single power supply.

Furthermore, the present disclosure offers advantages such as increasing effective plasma volume because uniform low-temperature plasma is generated through multiple plasma sources and providing a cold plasma generating apparatus optimized for use in applications related to sterilization.

As described above, although the exemplary embodiments have been described with reference to the limited drawings, those skilled in the art may apply various technical modifications and variations based on the above description. In the exemplary embodiments, appropriate results can be achieved even when the described technique may be performed in a different order from the described method and/or the elements of the described system, structure, device, circuit and the like may be combined in a different form or replaced or substituted by other elements or equivalents.

The embodiment described in the present specification and the attached drawings are merely illustrative for describing part of the technical spirit included in the present invention. Accordingly, the embodiment disclosed in the present specification is not intended to be limiting but is merely a description of the technical spirit of the present invention. Thus, it is apparent that the scope of the technical spirit of the present invention is not limited by this embodiment. It should be interpreted that other modifications and specific embodiments which those with ordinary knowledge in the art can easily infer within the scope of the technical spirit included in the specification and drawings of the present invention also fall within the technical scope of the present invention.

What is claimed is:

1. A cold plasma generating apparatus for generating a cold plasma source, the cold plasma generating apparatus comprising:
    an apparatus housing with a discharge hole formed at one end;
    a center conductor of conductive material provided along a longitudinal centerline of the apparatus housing;
    a nipple member provided at one side of the apparatus housing and connected to a cavity of the apparatus housing so that plasma gas enters the cavity;
    a microwave transmission member that extends integrally in a direction perpendicular to one side of the center conductor and transmits microwaves from a microwave generator to the center conductor; and
    an impedance matching adjustment member provided at the other end of the apparatus housing, for adjusting a length of the center conductor exposed to the cavity of the apparatus housing to minimize microwave reflection and match cavity impedance to a microwave source,
    wherein:
    the impedance matching adjustment member is configured as a knob-type adjustment member whose outer edge is threaded to the other end of the apparatus housing; and
    the other end of the center conductor is movably contained in the impedance matching adjustment member to be movable in and out of the impedance matching adjustment member, or the other end of the center conductor is threaded to the impedance matching adjustment member, and
    wherein the distance between the center conductor and the impedance matching adjustment member relative to the microwave transmission member is greater than one-quarter of the wavelength of the microwaves and less than one half of the wavelength of the microwaves.

2. The cold plasma generating apparatus of claim 1, wherein the discharge hole of the apparatus housing is larger than an outer diameter of the center conductor, and the outer diameter of the center conductor is smaller than a diameter of the discharge hole.

3. The cold plasma generating apparatus of claim 1, wherein the microwave transmission member has the same diameter as the center conductor and extends integrally and perpendicularly to the other end of the center conductor, and the microwave transmission member extends along a centerline of a tubular extension that has the same diameter as the apparatus housing and extends perpendicularly to the apparatus housing.

4. The cold plasma generating apparatus of claim 3, wherein the diameter of the center conductor is ½ of that of the microwave transmission member, the diameter of the microwave transmission member is ⅛ or less of a wavelength of the microwaves, and the length of the center conductor from the microwave transmission member to the other end of the apparatus housing is one-half or whole of the wavelength of the microwaves.

5. A multi-cold plasma array apparatus comprising:
    a treatment chamber having an inner space;
    a treatment target containing member provided in the inner space of the treatment chamber, where a treatment target is placed;
    a rotary agitator configured to rotate the treatment target containing member;
    multiple cold plasma generating apparatuses arranged in the treatment chamber;
    an ignition unit configured to ignite the multiple cold plasma generating apparatuses;
    a power supply configured to supply power to the multiple cold plasma generating apparatuses;

a power distribution unit configured to distribute a power supplied from the power supply uniformly to the multiple cold plasma generating apparatuses; and a gas circulation and supply unit configured to circulate and supply a gas or gas mixture to the treatment chamber, wherein each of the multiple cold plasma generating apparatuses comprises an apparatus housing with a discharge hole formed at one end;

a center conductor of conductive material provided along a longitudinal centerline of the apparatus housing;

a nipple member provided at one side of the apparatus housing and connected to a cavity of the apparatus housing so that plasma gas enters the cavity;

a microwave transmission member that extends integrally in a direction perpendicular to one side of the center conductor and transmits microwaves from a microwave generator to the center conductor; and an impedance matching adjustment member provided at the other end of the apparatus housing, for adjusting a length of the center conductor exposed to the cavity of the apparatus housing to minimize microwave reflection and match cavity impedance to a microwave source, wherein the power distribution unit comprises:

a nascent load that is connected to the power supply through a waveguide and receives initial microwave power from the power supply;

a microwave circulator that is provided on the waveguide, receives microwave power from the power supply, and redirects reflected waves of the microwave power back to the nascent load; and a power splitter that receives the microwave power, splits the received microwave power in multiple ways, and transmits the same split microwave power to each of the multiple plasma generating apparatuses, and the gas circulation and supply unit comprises:

a pumping device for pumping a gas and/or gas mixture out of the treatment chamber;

a filtering device for filtering the gas pumped out by the pumping device; and a gas adding device that adds the gas filtered by the filtering device and the gas supplied from an external gas supply device and feeds the gases to the cold plasma generating apparatus.

6. The multi-cold plasma array apparatus of claim 5, wherein the treatment target containing member is made of Teflon or fiberglass netting, the multiple cold plasma generating apparatuses are arranged toward a center of the treatment chamber to face each other, and the ignition unit comprises:

a grounded box formed with a cradle in which each of the multiple plasma generating apparatuses is tightly held and mounted;

a leaf spring that elastically supports the cold plasma generating apparatus and is electrically grounded to the grounded box;

a push switch provided on one side of the grounded box which can be depressed;

a relay provided on the push switch and comprising a shaft extendable by the relay;

an operating lever configured to be rotated by the shaft of the relay, having one end movable toward a tip of the multiple plasma generating apparatus, and having the other end connected to an output of the power supply; and a tension spring configured to elastically return the operating lever to the original position.

* * * * *